US006261545B1

(12) United States Patent
Okamoto

(10) Patent No.: US 6,261,545 B1
(45) Date of Patent: Jul. 17, 2001

(54) OPHTHALMIC COMPOSITIONS OF NEUROTROPHIC FACTORS, REMEDIES FOR OPTIC NERVE FUNCTION DISORDERS AND METHOD FOR TREATING OPTIC NERVE FUNCTION DISORDERS

(75) Inventor: Shinseiro Okamoto, Tokyo (JP)

(73) Assignee: Advanced Medicine Research Institute, Tokyo (JP)

( * ) Notice: Subject to any disclaimer, the term of this patent is extended or adjusted under 35 U.S.C. 154(b) by 0 days.

(21) Appl. No.: 09/254,587
(22) PCT Filed: Sep. 12, 1997
(86) PCT No.: PCT/JP97/03241
  § 371 Date: Mar. 10, 1999
  § 102(e) Date: Mar. 10, 1999
(87) PCT Pub. No.: WO98/10785
  PCT Pub. Date: Mar. 19, 1998

(30) Foreign Application Priority Data

Sep. 13, 1996 (JP) .................................... 8-243179

(51) Int. Cl.⁷ .................................................. A61K 31/74
(52) U.S. Cl. ...................... 424/78.04; 514/912; 514/913
(58) Field of Search .................... 424/78.04; 514/912, 514/913

(56) References Cited

U.S. PATENT DOCUMENTS

| | | |
|---|---|---|
| 5,270,051 | 12/1993 | Harris . |
| 5,349,056 | 9/1994 | Panayotatos . |
| 5,641,749 | 6/1997 | Yan et al. . |
| 5,641,750 | 6/1997 | Louis . |
| 5,667,968 | 9/1997 | LaVail et al. . |

FOREIGN PATENT DOCUMENTS

| | | |
|---|---|---|
| 219207 | 4/1987 | (EP) . |
| 443809 | 8/1991 | (EP) . |
| 57-203440 | 12/1982 | (JP) . |
| WO93/25684 | 12/1993 | (WO) . |
| WO95/26363 | 10/1995 | (WO) . |
| WO96/06859 | 7/1996 | (WO) . |
| WO97/34586 | 9/1997 | (WO) . |

OTHER PUBLICATIONS

Olivia Bermingham–McDonogh, Kathryn L. McCabe and Thomas A. Reh, "Effects of GGF/neuregulins on Neuronal Survival and Neurite Outgrowth Correlate with erbB2/neu Expression in Developing Rat Retina", *Development*, 122, 1427–1438, (1996).

Ramesh C. Tripathi, Navaneet S.C. Borisuth and Brenda J. Tripathi, "Growth Factors in the Aqueous Humor and Their Therapeutic Implications in Glaucoma and Anterior Segment Disorders of the Human Eye", *Drug Development Research*, 22:1–23 (1991).

*Primary Examiner*—Carlos A. Azpuru
(74) *Attorney, Agent, or Firm*—Frishauf, Holtz, Goodman, Langer & Chick, P.C.

(57) ABSTRACT

An ophthalmic composition which comprises a neurotrophic factor, an optic nerve functional disorder-treating agent which comprises a neurotrophic factor, and a method for treating an optic nerve functional disorder, which comprises administering an effective amount of a neurotrophic factor, particularly a glaucoma-treating agent and a method for treating the same are provided.

30 Claims, 3 Drawing Sheets

OPHTHALMIC COMPOSITIONS OF NEUROTROPHIC FACTORS, REMEDIES FOR OPTIC NERVE FUNCTION DISORDERS AND METHOD FOR TREATING OPTIC NERVE FUNCTION DISORDERS

This application is a U.S. national phase application under 35 U.S.C. 371 of PCT application number PCT/JP97/03241, filed Sep. 12, 1997.

TECHNICAL FIELD

This invention relates to an ophthalmic composition and an optic nerve functional disorder-treating agent which contain a neurotrophic factor, a contact lens into which this is formulated, and a method for treating an optic nerve functional disorder. More specifically, it relates to an ophthalmic composition, a treatment agent and a treatment method particularly effective for treating glaucoma.

BACKGROUND ART

Recently, it is said that one person per 30 to 40 persons of forty years and over suffers from glaucoma. Patients with this glaucoma tend to be increased every year, and glaucoma becomes a serious problem in the society where the aged is being increased. Therefore, establishment of a method for treating glaucoma which has not been established in the prior art has an important meaning, and also, a treatment agent effective for this glaucoma has been demanded.

Glaucoma is an optic nerve functional disorder caused by pressing an optic nerve by an optic disk which is an entrance and exit of an eyeball due to raising of intraocular pressure to cause a functional disorder. It is also considered that raising of intraocular pressure becomes a trigger of apoptosis of an optic nerve to cause an optic nerve functional disorder.

In conventional treatment of glaucoma, only intraocular pressure has been lowered by the dropping of a β-blocker in the eyes or internal application of an the intraocular presurelowering agent. However, even when the intraocular pressure is lowered, the lowering of eyesight and the stricture of a visual field continue to proceed and cannot be prevented even by administering vitamin $B_{12}$ and a blood stream-improving agent in some cases.

Therefore, the lowering of intraocular pressure is insufficient, and a medicine which takes charge of functional maintenance, improvement, growth and regeneration of an optic nerve itself is required for treatment of an optic nerve functional disorder. Also, a medicine for preventing apoptosis of an optic nerve is required.

SUMMARY OF THE INVENTION

In order to solve the above problem, the present inventor has found an ophthalmic composition and an optic nerve functional disorder-treating agent which contain a neurotrophic factor, a contact lens into which this is formulated, and a method for treating an optic nerve functional disorder using them, to accomplish the present invention.

An object of the present invention is to provide an ophthalmic composition which is useful for treating an optic nerve functional disorder, particularly glaucoma by preventing apoptosis and directly acting on an optic nerve. Another object of the present invention is to provide an ophthalmic composition which is useful for treating an optic nerve functional disorder, particularly glaucoma with less side effects.

Also, an object of the present invention is to provide an ophthalmic composition which can treat an optic nerve functional disorder by a simple and easy administration method without casting a heavy burden upon a patient and a doctor. Further, an object thereof is to provide a contact lens into which this is formulated. Additionally, an object thereof is to provide a method for treating an optic nerve functional disorder by administering these ophthalmic compositions.

The present invention relates to an ophthalmic composition which comprises a neurotrophic factor.

Also, the present invention relates to an optic nerve functional disorder-treating agent which comprises a neurotrophic factor.

Further, the present invention relates to a method for treating an optic nerve functional disorder, which comprises administering an effective amount of a neurotrophic factor.

BEST MODE FOR PRACTICING THE INVENTION

Figure 1:
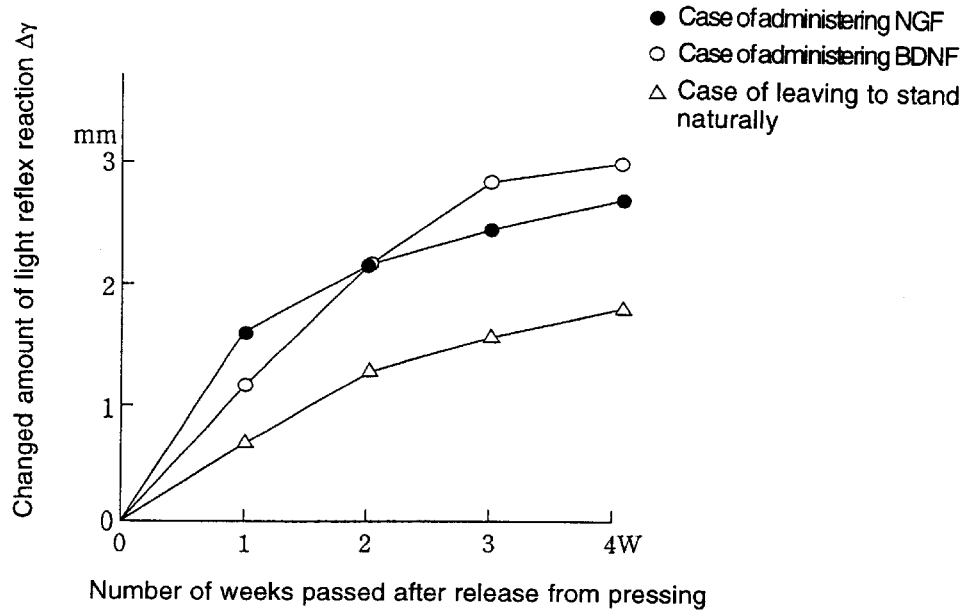
FIG. 1 is a showing a relation between a changed amount of a light reflex reaction and the number of weeks passed after release from pressing according to a Test example of the present invention.

The ophthalmic composition of the present invention may be used in either preparation form of an ophthalmic injection (an agent for subconjunctival injection, an agent for ocular injection and an agent for intraocular injection), an ophthalmic agent for external application (an agent for dropping in eyes and an agent for an ophthalmic ointment), an agent for internal application, an agent for intravenous injection, an agent for intramuscular injection and an agent for subcutaneous injection. However, in particular, in consideration of alleviation of side effects, simplicity and easiness of administration, efficient transition of a medicine to a diseased part and the like, a preparation form for site-specific administration to eyes is preferred, and an agent for dropping in eyes and an agent for an ophthalmic ointment are particularly preferred.

The neurotrophic factor in the present invention is not particularly limited so long as it is a factor having actions of differentiation, protection and regeneration of a nerve. These neurotrophic factors may be used alone or as a mixture of two or more of them. As such a neurotrophic factor, for example, NGF (a nerve growth factor), BDNF (a brain-derived neurotrophic factor), CNTF (a ciliary neurotrophic factor), NT-3 (neurotrophin-3), NT-4/5 (neurotrophin-4/5), NT-6 (neurotrophin-6), GDNF (a gliacytederived neurotrophic factor), AF-1 (an axogenesis factor), GGF2 (a glia growth factor) and derivatives thereof are preferred, NGF and BDNF are more preferred, and BDNF is particularly preferred. Here, the above NGF is a first neurotrophic factor found by Levi-Montaltini et al. in Italy.

The above neurotrophic factor is a general name of proteins which perform maintenance, growth and differentiation of neurocytes, and each of NGF and BDNF is one of them.

When the neurotrophic factor is used as an ophthalmic solution or an agent which is to be administered in the form of being absorbed into a contact lens, in order to adjust it so as to have a composition close to that of an intraocular liquid or an aqueous humor, pharmaceutically acceptable various additives, for example, an isotonicity-imparting agent, a buffer and the like may be added, if necessary.

As these additives, specifically, glucose, sodium chloride, potassium chloride, calcium chloride, magnesium sulfate, sodium hydrogen carbonate, glutathione and the like may be added, but the present invention is not limited thereby.

As the optic nerve functional disorder in the present invention, there may be mentioned, for example, an optic nerve functional disorder caused by pressing an optic nerve due to fracture of an optic fasciculus duct or an intraorbital abscess and arteriovenous aneurysm; an intracranial disease; a cerebral tumor; a pituitary tumor, an optic nerve functional disorder caused by hemorrhage, interruption of blood circulation or infarction, a glaucomatous optic nerve disease and the like.

As glaucoma to which the present invention is to be applied, there may be mentioned low tension glaucoma (normal tension glaucoma; particularly in this case, it can be said that it is a functional disorder of an optic nerve itself also, apoptosis is also considered), high tension glaucoma (open-angle glaucoma or narrow-angle glaucoma (acute inflammatory glaucoma), congenital glaucoma and secondary glaucoma) and the like, but the present invention is not limited thereby, and the effect of the present invention exhibits in all kinds of optic nerve functional disorders other than the above, particularly glaucoma.

In the ophthalmic composition of the present invention, additives and a base which have been known in this field of the art are used suitably.

The case where it is prepared as an ophthalmic solution and an ophthalmic ointment is explained below.

The amount of the neurotrophic factor to be used is not particularly limited, and it may be about 0.0001 to 0.5% (W/V) (or $10^{-3}$ to $2\times10^5$ µg/l), particularly preferably 0.0004 to 0.04% (or $10^{-1}$ to $1\times10^3$ µg/l) in a prepared medicine. Also, an isotonicity-imparting agent, a base, a pH adjuster, a viscosity-imparting agent, a suspending agent, an emulsifier, a preservative and pharmaceutically acceptable additives can be added, if necessary.

The ophthalmic solution in the present invention may be either of an aqueous ophthalmic solution, a non-aqueous ophthalmic solution, a lyophobic ophthalmic solution and a lyophilic ophthalmic solution. In this case, in general, the ophthalmic solution is roughly classified into a case of using an aqueous solvent and a case of using a nonaqueous solvent.

As the aqueous solvent to be used in the present invention, there may be mentioned, for example, a solvent such as sterilized purified water, physiological saline and the like, and a solvent containing various kinds of components necessary for an ophthalmic solution, including various kinds of electrolytic ions such as BSS plus (trade name, produced by Alcon Co.) and the like, a buffer, an isotonicity-imparting agent, glutathione, glucose and the like, or a solvent containing vitamin B12. Also, as the non-aqueous solvent, there may be mentioned, for example, vegetable oils such as cottonseed oil, soybean oil, sesame oil, peanut oil, castor oil, olive oil, camellia oil, rapeseed oil and corn oil, fluid paraffin and the like.

The above isotonicity-imparting agent is not limited so long as it is used in this field of the art, and sodium chloride, boric acid, potassium nitrate, D-mannitol, glucose and the like are preferred. Its amount to be used may be 0.6 to 2.0 in terms of an osmotic pressure ratio.

The above pH adjuster is not limited so long as it is used in this field of the art, and boric acid, anhydrous sodium sulfite, hydrochloric acid, sodium hydroxide, sodium citrate, acetic acid, potassium acetate, sodium carbonate, sodium hydrogen carbonate, borax, a buffer (e.g., a citrate buffer, a phosphate buffer, etc.) and the like are particularly preferred. Its amount to be used may be an amount by which the pH of the ophthalmic composition can be adjusted to 3.0 to 8.0.

The above viscosity-imparting agent is not limited so long as it is used in this field of the art, and methyl cellulose, hydroxypropyl cellulose, hydroxypropylmethyl cellulose, polyvinyl alcohol, sodium chondroitin sulfate, polyvinyl pyrrolidone and the like are particularly preferred. Its amount to be used may be an amount by which viscosity enough to be dropped from an ophthalmic solution bottle can be imparted, and it may be, for example, 0.001% to 10% (W/V).

The above suspending agent is not limited so long as it is used in this field of the art, and Polysorbate 80 (trade name), polyoxyethylene hardened castor oil, polyoxy hardened castor oil, carboxymethyl cellulose and the like are particularly preferred. Its amount to be used may be 0.001% to 10% (W/V).

The above emulsifier is not limited so long as it is used in this field of the art, and yolk lecithin, Polysorbate 80 and the like are particularly preferred. Its amount to be used may be 0.001% to 10% (W/V).

The above preservative is not limited so long as it is used in this field of the art, and benzalkonium chloride, benzethonium chloride, chlorobutanol, phenylethyl alcohol, paraoxybenzoate and the like are particularly preferred. Its amount to be used may be 0.001% to 10% (W/V).

The above pH adjuster to be used in the ophthalmic ointment in the present invention is not limited so long as it is used in this field of the art, and boric acid, anhydrous sodium sulfite, hydrochloric acid, sodium hydroxide, sodium citrate, acetic acid, potassium acetate, sodium carbonate, sodium hydrogen carbonate, borax, a buffer (e.g., a citrate buffer, a phosphate buffer, etc.) and the like are particularly preferred. Its amount to be used may be an amount by which the pH of the ophthalmic composition can be adjusted to 3.0 to 8.0.

The base is not limited so long as it is used in this field of the art, and petrolatum, gelatinized hydrocarbon, polyethylene glycol, purified lanolin and the like are particularly preferred.

When the ophthalmic composition of the present invention is administered, an amount to be administered and the time of administration may be suitably increased or decreased depending on a preparation form to be used, a disease condition of a patient and the like. However, when the ophthalmic solution or the ophthalmic ointment is administered, a prepared medicine containing about 0.0001 to 0.5% (W/V) of the neurotrophic factor in the medicine may be administered by dropping in eyes or administered by application once to several times a day.

Also, by formulating or absorbing the optic nerve diseasetreating agent of the present invention into a composition of a contact lens, an optic nerve disease can be treated/prevented while a patient wears a contact lens.

EXAMPLES

In the following, the effect of the present invention is explained, but the present invention is not limited thereby.

Preparation Example 1

10 μg of NGF (produced by Pepro Tech EC Co.) was dissolved in 250 ml of BSS plus (trade name, produced by Alcon Co.) to obtain an ophthalmic solution.

Preparation Example 2

10 μg of BDNF (produced by Pepro Tech EC Co.) was dissolved in 250 ml of BSS plus (trade name, produced by Alcon Co.) to obtain an ophthalmic solution.

Preparation Example 3

5 μg of NGF (produced by Pepro Tech EC Co.) was dissolved in 250 ml of BSS plus (trade name, produced by Alcon Co.) to obtain an ophthalmic solution.

Preparation Example 4

5 μg of BDNF (produced by Pepro Tech EC Co.) was dissolved in 250 ml of BSS plus (trade name, produced by Alcon Co.) to obtain an ophthalmic solution.

Preparation Example 5

5 μg of NT-3 (produced by Research Biochemical International Co.) was dissolved in 250 ml of BSS plus (trade name, produced by Alcon Co.) to obtain an ophthalmic solution.

Preparation Example 6

5 μg of NT-4 (produced by Research Biochemical International Co.) was dissolved in 250 ml of BSS plus (trade name, produced by Alcon Co.) to obtain an ophthalmic solution.

Preparation Example 7

5 μg of CNTF (produced by R & D Systems Co.) was dissolved in 250 ml of BSS plus (trade name, produced by Alcon Co.) to obtain an ophthalmic solution.

Preparation Example 8

0.001 g of BDNF, 0.9 g of sodium chloride and 0.003 g of benzethonium chloride were dissolved in 100 ml of sterilized purified water. Then, the resulting solution was sterilized by filtration using a membrane filter to obtain an ophthalmic solution.

Preparation Example 9

0.001 g of BDNF was dissolved in 10 ml of sterilized purified water, and the solution was sterilized by filtration using a membrane filter and then lyophilized to obtain powder. Then, 100 g of plastibase and 0.01 g of chlorobutanol were added to the powder obtained, and the mixture was kneaded by a motar to obtain an ophthalmic ointment.

Test Example 1

It is considered that glaucoma is caused by pressing an optic nerve by an optic disk which is an entrance and exit of an eyeball due to raising of intraocular pressure to cause a functional disorder. Also, the route of a light reflex reaction of a pupil is an eye→an optic nerve (a centripetal route)→a center→a parasympathetic nerve (a centrifugal route)→an iris, and the disorder of an optic nerve caused by glaucoma is a centripetal route disorder and is shown by lowering of a light reflex reaction. Therefore, in this test, the treatment effects of the ophthalmic compositions of the present invention were confirmed by using colored rabbits in which light reflex reactions of pupils to stimulating light were weakened by raising intraocular pressures to cause an optic nerve functional disorder and measuring the respective light reflex reactions of the pupils.

In order to raise intraocular pressure, a ring-shaped corneoscleral ring portion-sucking apparatus was prepared. This ring-shaped suction apparatus was put on a corneoscleral portion at the outside of an angle, suction was performed, and closing of the angle was caused to raise intraocular pressure (This is a known method used for an ophthalmodynamometer or the like in the region of ophthalmology.). As a suction pump used in said apparatus, "EC5000 Aspiration Unit (trade name)" manufactured by Nidek Co., Ltd. was used, and the outer portion of the angle was sucked at a negative pressure of 70 cmHg to raise intraocular pressure to 60 mmHg.

As a source of the stimulating light for measuring a light reflex reaction, a Neitz Brite Scope was used.

A convex lens of +14D was placed in front of an eye at a distance of 7 cm, and the eye was irradiated with light which was once converged and then scattered to uniformly irradiate a wide range of an eyeground in an open loop state.

In this test, the maximum value (max.) of each light reflex reaction was measured by irradiating the eye of the rabbit with light from a slightly lower portion. Recording was performed by using "macropolaphy auto 6 (trade name)" manufactured by Polaroid Co.

By using the above the intraocular pressure-raising apparatus, light stimulating apparatus and pupil diameter-measuring method, an optic nerve functional disorder due to raising of intraocular pressure was judged, and judgment of the treatment effects of the ophthalmic compositions of the present invention was performed.

Specifically, suction was performed for 9 hours twice a day in the morning and in the afternoon except for discontinuing suction for 1 hour at the time of feeding the rabbits. Almost no weakening of the light reflex reactions to the stimulating light was observed when suction was performed for one week and two weeks, but weakenings thereof were observed at the third week. Suction was discontinued when suction was performed for one month, and the progresses of changes in the light reflex reactions were observed every week for one month. After the rabbits were released from suction, the ophthalmic compositions (Preparation examples 1 and 4) of the present invention were administered by dropping in the eyes in an amount of one drop to several drops four times a day. The administered liquid medicine is absorbed from a cornea and transited to an anterior aqueous humor, a part thereof reaches an optic disk through a Cloquet tube and shows an effect in nerve fibers, a part thereof is scattered in a corpus vitreum and reaches an optic nerve. Also, a part thereof passes an unconventional route of an anterior aqueous humor (From a series of studies using various kinds of tracers by Bill, A et al., an intraocular circulation route of an anterior aqueous humor, in which an anterior aqueous humor passes an iris and a ciliary body and reaches a choroidsuprachoroidal space, has been confirmed other than a common conventional route in which an anterior aqueous humor is excreted from an angle.), reaches an optic nerve and shows an effect. It has been confirmed by Colo (Exp. Eye. Res. 23:57–585) et al. that this intraocular circulation route exists also in a rabbit. A route other than the routes mentioned here may be considered. A treatment effect (a recovery degree) was determined by measuring the light reflex reaction immediately after the rabbit was released from suction, using a pupil diameter at this time as a standard value, subtracting a value of a pupil diameter showing a recovered light reflex reaction with the lapse of time from the standard value and defining a changed amount of the light reflex reaction as Δγ.

These results are shown in FIG. 1.

As can be clearly seen from FIG. 1, the light reflex reaction is gradually recovered even when the rabbit is left to stand naturally. However, the ophthalmic compositions of the present invention were administered, remarkable recovery effects were observed.

It can be understood that the treatment effects by the ophthalmic compositions of the present invention were shown in one week, and the functions of the optic nerves were gradually recovered with the lapse of time. Also, it was confirmed that the effect of BDNF was strong.

Test Example 2

With respect to the eyes of rabbits having reduced visual evoked potentials (VEP), in each of which an optic nerve functional disorder was caused due to raising of intraocular pressure, the treatment effects of the ophthalmic compositions of the present invention were confirmed.

A ring-shaped corneosclera-sucking apparatus was prepared and put on each left eye of colored rabbits and white rabbits, and a corneosclera was sucked in a ring state from the peripheral portion of a cornea by an air pump non-noise S500 (trade name, manufactured by Nippon Dobutsu Yakuhin) so that intraocular pressure was raised to 60 mmHg. Raising of the intraocular pressure was confirmed by a simplified Shoiotz tonometer (manufactured by Chiron Co.).

Suction was performed for 8 hours a day and discontinued for 1 hour for feeding and water supply.

VEPs of the rabbits were measured after completion of suction using the suction ring and the next morning, and at the time when the reduced potentials were not recovered the next morning, droppings in the eyes of the ophthalmic compositions of the present invention were started.

VEP was measured by using a Nerupack 2 evoked potential tester MEB-7102 (trade name, manufactured by Nippon Kodensha) according to the following method (a flash VEP method using 2 channels).

Induced electrodes (−) were subcutaneously pierced and fixed at a left side of an occipital region of each rabbit (channel 1, a right eye-stimulating potential) and at a right side of the occipital region (channel 2, a left eyestimulating potential), standard electrodes (+) were fixed to ears (left and right electrodes are connected), and further earth electrodes were fixed to a forehead portion. Next, the rabbit was dark-adapted, and measurement was performed under the following measurement conditions.

Amplified recording sensitivity
    channel 1 20 $\mu$V/diV
    channel 2 20 $\mu$V/diV
    high frequency filter 100 Hz
    low frequency filter 1 Hz
Analysis time 200 msec
Addition average time 200 times
Flash stimulation flash frequency 1 Hz
    light emission amount 0.6 J
    distance 20 to 30 cm After light stimulation, the potential of a peak portion which appeared by 30 msec was measured, and reduction or recovery of VEP was shown by % with a normal time (before suction was started) being defined as 100%.

VEP is a reaction which occurs in a cerebral cortex visual field when light stimulation is given to a retinal photoreceptor, and excitation caused in a retina is transited through an optic nerve and then an optic tract neuron to another neuron at an outside geniculate body and reaches a cerebral cortex visual field. Although stimulation from one eye is transited to left and right brains due to crossing of optic nerves in human, the optic nerves of a rabbit are completely crossed so that excitation of a left eye retina is all transited to a right brain visual field.

It has been known that VEP in a rabbit is obtained as peaks of a retina, an optic tract, an outside geniculate body and a visual cortex by a relatively early latent time (30 msec) after light stimulation (K. Koshino, et al., Neuroscience 14:23–27, 1988).

The neurotrophic factor ophthalmic solutions of Preparation examples 3 to 7 and a base ophthalmic solution (BSS plus, trade name) as a control were administered by dropping to the left eyes of the rabbits having reduced VEP in an amount of the respective one drop six times a day continuously for 21 days.

Measurement of VEP was performed once or twice everyday after treatment by the neurotrophic factors was started.

Figure 2:
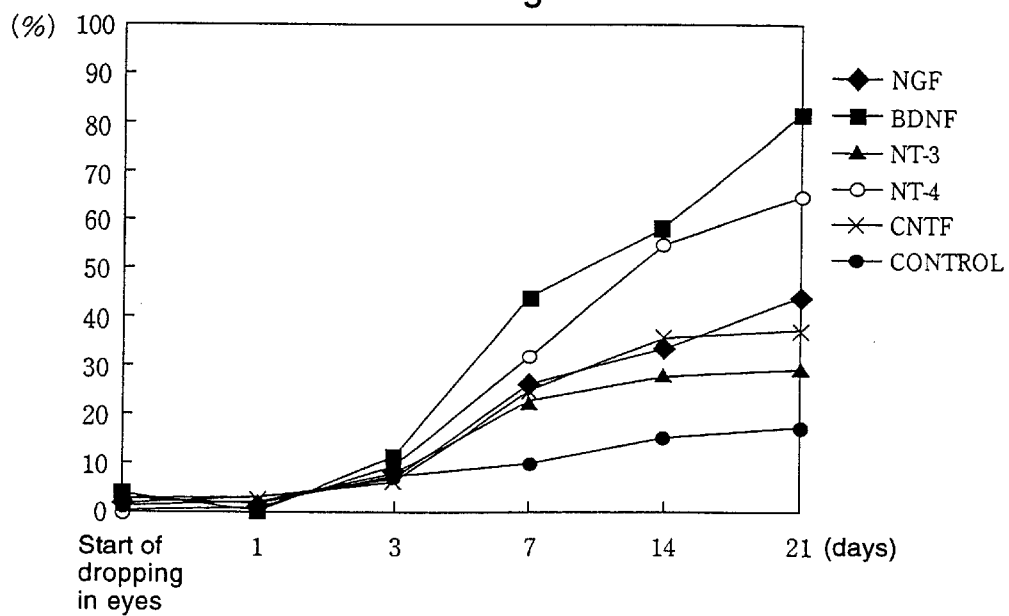
FIG. 2 is a graph showing treatment effects of neurotrophic factors on rabbit eyes in which optic nerves are damaged according to a Test example of the present invention.

The results are shown in FIG. 2.

In all of the rabbits to which the neurotrophic factors were administered by dropping in the eyes for 21 days, recovery of VEP with the lapse of time was observed. Even in the rabbit to which only the base as a control was administered by dropping in the eyes, recovery of VEP was observed, but a degree thereof was very light.

The optic nerve functions of the rabbits were recovered by the treatment effects of the ophthalmic compositions of the present invention, and the effects of BDNF and NT-4 were remarkable.

Text Example 3

With respect to a patient with low tension glaucoma (the eyesight and intraocular pressure of the patient before treatment were normal), a test of a treatment effect by administration of BDNF was performed.

Figure 3A:
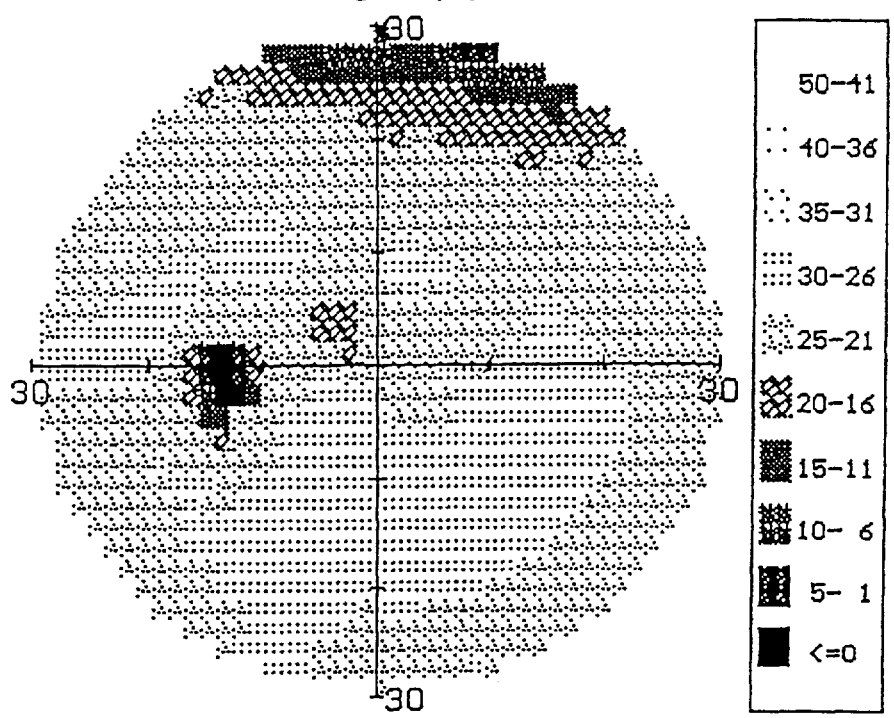
FIGS. 3(a) and (b) are views showing an effect of improving a visual field before and after administration of BDNF in Test example 3.

The visual field of the patient examined by a Dicon static perimeter before treatment is shown in FIG. 3(a). In an eyeground test, depression of an optic disk was remarkably observed. Also, in a visual field test, lowering of visual sensitivity and scotoma were observed.

Figure 3B:
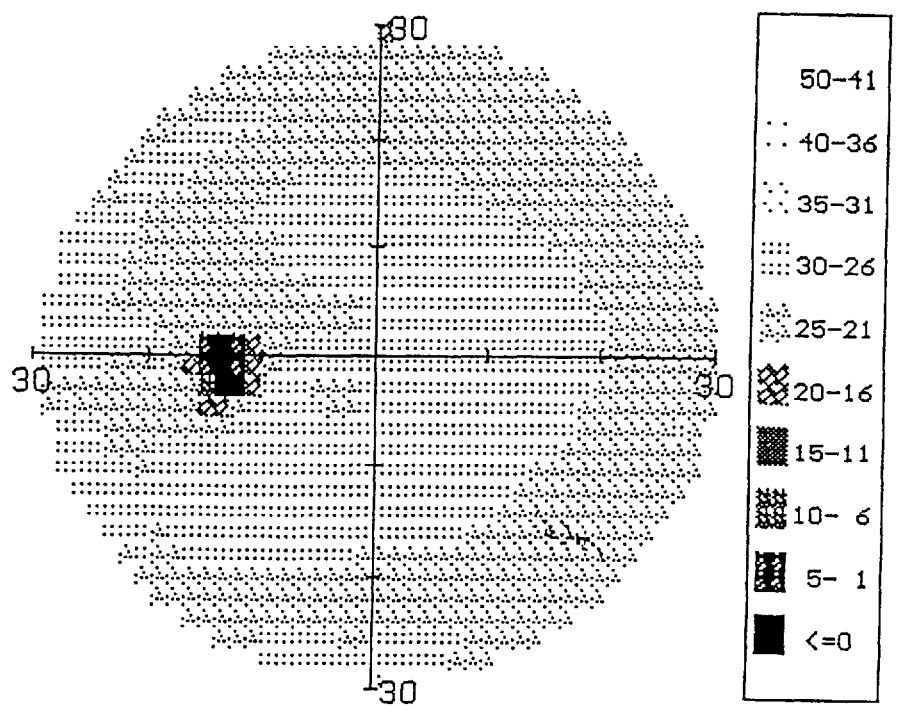

When BDNF (20 $\mu$g/l) prepared in Preparation example 4 was administered to this patient by dropping in the eyes at a rate of four times a day, an effect of improving the visual field was started to be shown in one week. After three weeks, as shown in FIG. 3(b), lowering of visual sensitivity was ameliorated, scotoma disappeared, and an excellent effect of BDNF was confirmed.

Test Example 4

With respect to a patient with narrow-angle glaucoma (acute inflammatory glaucoma attack), a test of a treatment effect by administration of BDNF was performed.

Figure 4A:
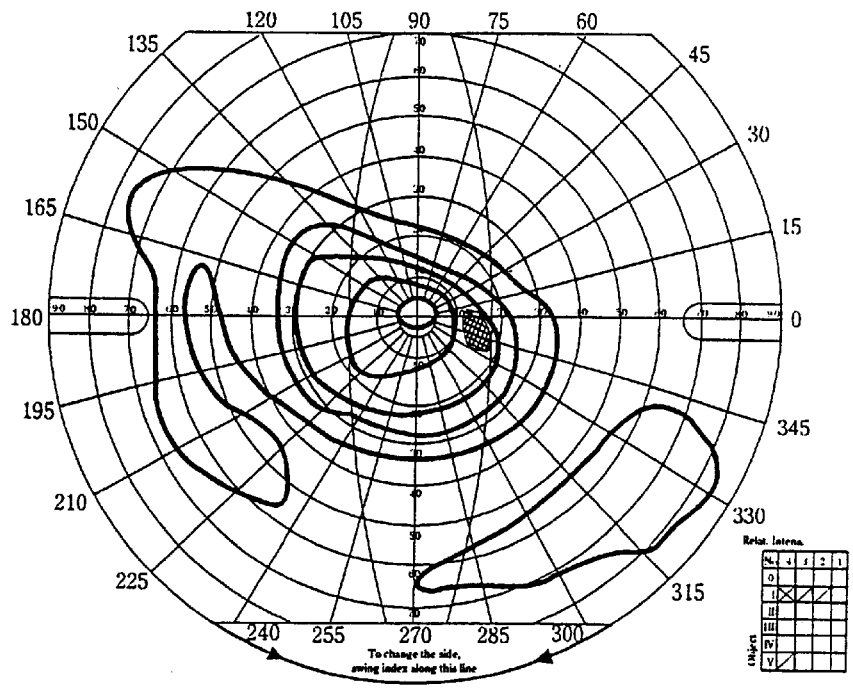
FIGS. 4(a) and (b) are views showing an effect of improving a visual field before and after administration of BDNF in Test example 4.

The visual field of the patient examined by a Goldmann kinetic perimeter before treatment is shown in FIG. 4(a). As can be clearly seen from the figure, deficiency of the visual field was observed.

Figure 4B:
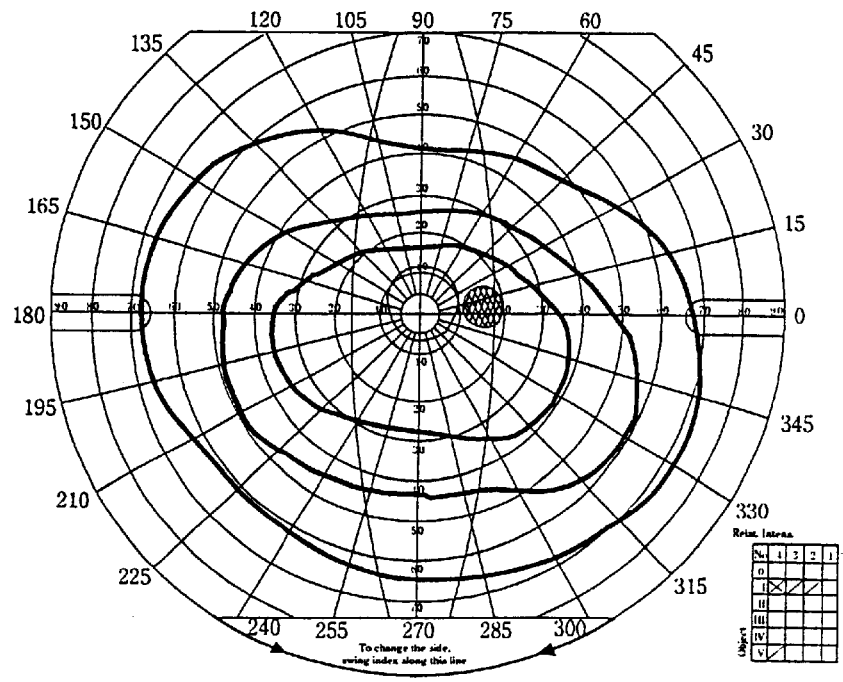

When BDNF (20 $\mu$g/l) prepared in Preparation example 4 was administered to this patient by dropping in the eyes at a rate of four times a day, deficiency of the visual field disappeared completely in about one month, and as shown in FIG. 4(b), the visual field was returned to a normal state. Thus, an excellent effect of BDNF was confirmed.

Test Example 5

With respect to a patient with low tension glaucoma, a test of a treatment effect by administration of NT-4/5 was performed.

When the visual field of the patient before treatment was examined by a Goldmann kinetic perimeter, stricture of the visual field was observed.

When NT-4/5 (20 μg/l) was administered to this patient by dropping in the eyes at a rate of four times a day, an effect of improving the visual field was started to be shown in two weeks. After about seven weeks, it was confirmed by a Goldmann kinetic perimeter that the visual field was enlarged to a substantially normal range.

Test Example 6

With respect to a patient with narrow-angle glaucoma, a test of a treatment effect by administration of NT-3 was performed.

When the visual field of the patient before treatment was examined by a Goldmann kinetic perimeter, stricture of the visual field was observed, and when it was examined by a static perimeter (octopus 1-2-3, trade name), lowering of visual sensitivity and stricture of the visual field were observed in both of the eyes.

When NT-3 (20 μg/l prepared in Preparation example 5 was administered to this patient by dropping in the eyes at a rate of four times a day, an effect exhibited and the visual field was enlarged at the second week. Also, after about two months, the visual field was recovered to a substantially normal range. The kinetic visual field of the right eye became normal, that of the left eye was also improved, the static visual field of the right eye became normal, that of the left eye was improved, and the eyesight was also improved. Thus, an excellent effect of NT-3 was confirmed.

Test Example 7

With respect to a patient with open-angle glaucoma, a test of a treatment effect by administration of NGF was performed.

When the visual field of the patient before treatment was examined by a Goldmann kinetic perimeter, stricture of the visual field was observed, and only 40° of the visual field at a lower half portion was left in the right eye.

When NGF (40 μg/l) prepared in Preparation example 1 was administered to this patient by dropping in the eyes at a rate of four times a day, an effect exhibited and the visual field was improved from a peripheral portion thereof at the first week. Also, after about one month, the visual field was considerably enlarged, and after about six months, the visual field was improved to be a considerably wide range. Thus, an excellent effect of NGF was confirmed.

Utilizability in Industry

A neurotrophic factor binds specifically to a neurotrophic factor receptor and exhibits an effect by directly acting on an optic nerve. As a result, the neurotrophic factor has advantages that almost no side effect is caused, it can be administered directly to an eyeball, and general administration can be also performed.

The ophthalmic composition of the present invention is useful for preventing apoptosis and treating an optic nerve functional disorder, particularly glaucoma and has an advantage that less side effects are caused. Also, the ophthalmic composition of the present invention can treat an optic nerve functional disorder by a simple and easy administration method without casting a heavy burden upon a patient and a doctor. Further, a contact lens into which the composition of the present invention is formulated can treat an optic nerve functional disorder similarly. Furthermore, in the present invention, a method for treating an optic nerve functional disorder by administering these ophthalmic compositions is provided.

What is claimed is:

1. An ophthalmic composition for treating glaucoma by external administration which comprises an effective amount of a brain-derived neurotrophic factor for treating glaucoma in combination with a pharmaceutically acceptable carrier, wherein the composition is a form selected from the group consisting of an ophthalmic solution and an ophthalmic ointment and wherein the composition includes at least one agent selected from the group consisting of an isotonicity-imparting agent, a viscosity-imparting agent, a suspending agent, an emulsifier, a preservative and a pH adjuster.

2. The ophthalmic composition according to claim 1, wherein the composition contains an isotonicity-imparting agent.

3. The ophthalmic composition according to claim 1, wherein the concentration of the isotonicity-imparting agent is 0.6 to 2.0 in terms of an osmotic pressure ratio.

4. The ophthalmic composition according to claim 1, wherein the composition contains a viscosity-imparting agent.

5. The ophthalmic composition according to claim 4, wherein the concentration of the viscosity-imparting agent is 0.001% to 10% (W/V).

6. The ophthalmic composition according to claim 1, wherein the composition contains a suspending agent.

7. The ophthalmic composition according to claim 6, wherein the concentration of the suspending agent is 0.001% to 10% (W/V).

8. The ophthalmic composition according to claim 1, wherein the composition contains an emulsifier.

9. The ophthalmic composition according to claim 8, wherein the concentration of the emulsifier is 0.001% to 10% (W/V).

10. The ophthalmic composition according to claim 1, wherein the composition contains a preservative.

11. The ophthalmic composition according to claim 10, wherein the concentration of the preservative is 0.0001% to 10% (W/V).

12. The ophthalmic composition according to claim 1, wherein the composition contains a pH adjuster.

13. The ophthalmic composition according to claim 12, wherein the composition contains a pH adjuster necessary for retaining pH at 3.0 to 8.0.

14. The ophthalmic composition according to claim 1, wherein the concentration of the neurotrophic factor is 0.0001 to 0.5% (W/V).

15. The ophthalmic composition according to claim 1, wherein the concentration of the neurotrophic factor is $10^{-3}$ to $2 \times 10^5$ μg/l.

16. A method for treating glaucoma which comprises administering to a patient in need thereof an effective amount of a brain-derived neurotrophic factor in the form of an ophthalmic composition for external administration selected from the group consisting of an ophthalmic solution and an ophthalmic ointment, wherein the ophthalmic composition contains at least one agent selected from the group consisting of an isotonicity-imparting agent, a viscosity-imparting agent, a suspending agent, an emulsifier, a preservative and a pH adjuster.

17. The method according to claim 16, wherein the ophthalmic composition contains an isotonicity-imparting agent.

18. The method according to claim 17, wherein the isotonicity-imparting agent is in a concentration of 0.6 to 2.0 in terms of an osmotic pressure ratio.

19. The method according to claim 16, wherein the ophthalmic composition contains a viscosity-imparting agent.

20. The method according to claim 19, wherein the viscosity-imparting agent is in a concentration of 0.001% to 10% (W/V).

21. The method according to claim 16, wherein the ophthalmic composition contains a suspending agent.

22. The method according to claim 21, wherein the suspending agent in is in a concentration of 0.001% to 10% (W/V).

23. The method according to claim 16, wherein the ophthalmic composition contains an emulsifier.

24. The method according to claim 23, wherein the emulsifier is in a concentration of 0.001% to 10% (W/V).

25. The method according to claim 16, wherein the ophthalmic composition contains a preservative.

26. The method according to claim 25, wherein the preservative is in a concentration of 0.0001% to 10% (W/V).

27. The method according to claim 16, wherein the ophthalmic composition contains a pH adjuster.

28. The method according to claim 27, wherein the pH adjuster maintains a pH of 3.0 to 8.0.

29. The method according to claim 16, wherein the neurotrophic factor is in a concentration of 0.0001 to 0.5% (W/V).

30. The method according to claim 11, wherein the neurotrophic factor is in a concentration of $10^{-3}$ to $2 \times 10^5$ μg/l.

* * * * *